(12) United States Patent
Inamoto et al.

(10) Patent No.: US 8,658,625 B2
(45) Date of Patent: Feb. 25, 2014

(54) EXTERNAL PREPARATION FOR TREATING PAINFUL SKIN WOUND

(75) Inventors: Yukiko Inamoto, Takamatsu (JP); Mitsuhiro Kawada, Higashikagawa (JP); Akihiro Hasui, Sanuki (JP); Kenichi Hattori, Tokushima (JP)

(73) Assignee: Teikoku Seiyaku Co., Ltd., Kagawa-ken (JP)

( * ) Notice: Subject to any disclaimer, the term of this patent is extended or adjusted under 35 U.S.C. 154(b) by 686 days.

(21) Appl. No.: 10/589,462

(22) PCT Filed: Feb. 16, 2004

(86) PCT No.: PCT/JP2004/001619
§ 371 (c)(1),
(2), (4) Date: Aug. 14, 2006

(87) PCT Pub. No.: WO2005/077380
PCT Pub. Date: Aug. 25, 2005

(65) Prior Publication Data
US 2007/0197483 A1    Aug. 23, 2007

(51) Int. Cl.
*A61K 31/616* (2006.01)

(52) U.S. Cl.
USPC ........ 514/165; 514/887; 514/159; 424/78.02; 424/78.06

(58) Field of Classification Search
None
See application file for complete search history.

(56) References Cited

U.S. PATENT DOCUMENTS

| | | | |
|---|---|---|---|
| 4,126,681 A | 11/1978 | Reller | |
| 4,219,548 A * | 8/1980 | Reller | 514/786 |
| 5,376,376 A | 12/1994 | Li | |
| 5,487,899 A | 1/1996 | Davis | |
| 5,874,479 A | 2/1999 | Martin | |
| 5,916,918 A | 6/1999 | Konishi et al. | |
| 5,932,230 A | 8/1999 | DeGrate | |
| 6,268,355 B1 * | 7/2001 | Mizobuchi et al. | 514/165 |
| 6,284,797 B1 | 9/2001 | Rhodes | |
| 2003/0125307 A1 | 7/2003 | Inamoto et al. | |
| 2003/0125308 A1 | 7/2003 | Inamoto et al. | |
| 2003/0232094 A1 | 12/2003 | Fuller | |
| 2006/0045858 A1 | 3/2006 | Fuller | |

FOREIGN PATENT DOCUMENTS

| | | |
|---|---|---|
| EP | 0 784 975 | 7/1997 |
| JP | 64-3123 | 1/1989 |
| JP | 3-72426 | 3/1991 |
| NZ | 258129 | 10/1999 |
| WO | 01/70210 | 9/2001 |

OTHER PUBLICATIONS

Steen et al, Dose-dependent competitive block by topical acetylsalicylic and salicylic acid of low pH-induced cutaneous pain, Pain, 64 (1996) 71-82.*
Lee et al , Skin Injury in the operating room, Injury, vol. 29,. No. 5, paes 345-347, 1998.*
Baxter, Nursing Times, vol. 99, No. 13, 2003, pp. 1-5.*
Examination Report (in English) dated Feb. 5, 2009 issued in New Zealand patent application No. 549208 corresponding to the present U.S. application.
Supplementary European Search Report dated Dec. 23, 2009 in European Application No. 04 71 1488 corresponding to the present U.S. application.
Kay H. Steen et al., "Topical acetylsalicylic, salicylic acid and indomethacin suppress pain from experimental tissue acidosis in human skin", PAIN, vol. 62, No. 3, pp. 339-347, XP002560409, ISSN: 0304-3959, Sep. 1995.
M. Hyllested et al., "Comparative effect of paracetamol, NSAIDs or their combination in postoperative pain management: a qualitative review", British Journal of Anaesthesia, Feb. 2002, 88(2), pp. 199-212.

* cited by examiner

*Primary Examiner* — Savitha Rao
(74) *Attorney, Agent, or Firm* — Wenderoth, Lind & Ponack, L.L.P.

(57) ABSTRACT

External preparations for treatment of painful skin wound having an analgesic activity which comprises acetylsalicylic acid or its pharmacologically acceptable salt as an active ingredient.

2 Claims, No Drawings

EXTERNAL PREPARATION FOR TREATING PAINFUL SKIN WOUND

TECHNICAL FIELD

The present invention relates to an external preparation which together has a skin wound-healing effect and a pain-alleviating effect in the skin wound region in regard to skin wound associated with a pain, and therapeutic methods thereof.

In more detail, the present invention relates to an external preparation which shows an activity for alleviating a pain while treating skin wound when acetylsalicylic acid or its pharmacologically acceptable salt is administered for a patient suffered from painful skin wound as an active ingredient, and therapeutic methods thereof.

BACKGROUND ART

Although symptoms of various skin wounds caused by traumata, such as thermal burn, racoma, laceration and incised wound, infectious disease in surgery, postoperative wound, decubital ulcer, temperature impairment, chemical impairment, radiation injury, vessel and lymphangiopathy, and others have developed, these skin wounds are accompanied with a strong pain, in many cases.

Medication of a local anesthetic, short term medication of a steroid for external use, oral administration of a nonsteroidal anti-inflammatory drug, etc. are performed as treatment of a pain accompanying skin wound now. However, medication of the local anesthetic or the external steroid often retards wound healing, and there are anxious about side effects, such as gastric ulcer, in oral administration of a nonsteroidal anti-inflammatory drug.

Moreover, generally, since medication to wound region of a non steroidal anti-inflammatory agent retards wound-healing, such medication in the wound region is considered to be contraindication.

As such reason, in regard to alleviation of a pain associated with skin wound, the positive treatment is seldom performed about the pain accompanying skin wound, and the pain is usually put up with until the wound heals.

On the other hand, some therapeutic agents are developed as a wound healing drug. Although many of them have an action which promotes proud flesh proliferation, medication to the wound of the advanced stages in early stages of thermal burn, etc. may worsen its symptoms on the contrary.

Moreover, about what contains iodine among therapeutic agents for wound, the hypersensitivity to iodine is caused or retardation of wound-healing by the cytotoxicity of iodine, etc. is reported.

By the way, acetylsalicylic acid (it may be called hereafter aspirin) is mainly and widely used in the form of oral administration as an analgesic antipyretic for many years, owing to its powerful analgesic, antipyretic and anti-rheumatism activities, and is a medicine with high safety also with few side effects.

In recent years, the research on application to external preparations of acetylsalicylic acid is advanced.

As what indicated a new pharmacological activity as external preparations, moreover, ointments for treatment of neuralgia in Japanese Patent Publication A 3-72426, external preparations for skin injury in Japanese Patent Publication A 9-235232, dermal administration system for treatment of anti-thrombus and for prevention of cancer in Japanese Patent Publication (Toku Hyo Hei) 8-504198, external preparations for treatment of allergodermia in Japanese Patent Publication A 2001-187739, external preparations for antipruritics in WO 01/47525, etc. are mentioned, respectively.

However, there are no external preparations containing acetylsalicylic acid aiming at preventing a pain in the skin wound area, and that it is not indicated at all about the therapeutic effect of external preparations containing acetylsalicylic acid to the skin wound associated with a pain.

DISCLOSURE OF INVENTION

The purpose of the present invention is to solve above problems and is to provide a treating agent for skin wound containing acetylsalicylic acid as an active ingredient, which has few side effects, excels in an inhibitory effect over a pain of the skin wound region, and does not cause retardation of wound-healing.

The present inventors have extensively studied to solve the above problems and found that external preparations containing acetylsalicylic acid as an active ingredient have an excellent wound-healing effect, reduced side effects and further an activity alleviating a pain associated with the skin wound.

That is, in a postoperative pain-model animal which is one of animal models of skin wound associated with a pain, inhibition to the pain of the skin wound region by medication of an external-preparation containing acetylsalicylic acid was found out and that the wound-healing effect in a wound model animal was also confirmed.

Furthermore, although this activity and effect depends on the concentration of acetylsalicylic acid in a preparation, in excess of a certain fixed concentration of acetylsalicylic acid, the activity and effect hardly changes.

The present invention relates to external preparations for treatment of painful skin wound having also an analgesic activity, which contains as an active ingredient acetylsalicylic acid or its pharmacologically acceptable salt.

The present invention relates also to a method for treatment painful skin wound and for alleviating a pain which consists of medicating to an affected region of patients with an effective dose of a medicament which contains as an active ingredient acetylsalicylic acid or its pharmacologically acceptable salt.

BEST MODE FOR CARRYING OUT THE INVENTION

Acetylsalicylic acid contained in the external preparations of the present invention is listed in the Japanese Pharmacopoeia. The content of acetylsalicylic acid contained in the external preparations changes with forms of the preparation, and it is 0.01 to 80% by the total weight for exhibiting a sufficient effect, preferably 0.05 to 50% by the weight, and more preferably 0.01 to 70% by the weight.

Since inhibition of a pain and wound-healing action, when the content of acetylsalicylic acid is less than 0.01% by the weight, are not fully demonstrated, it is not desirable. Moreover, at 80% by the weight or more, it becomes difficult to manufacture the preparation containing acetylsalicylic acid.

Acetylsalicylic acid and its pharmacologically acceptable salt such as a salt formed with an amino acid, such as DL-lysine, or a mineral salt such as sodium salt can be used as the active ingredient contained in the external preparations of the present invention.

Especially if the external preparations of the present invention are such a dosage form as an active ingredient is administered directly to the local surface of the skin, they will not be limited, and for example, ointments, ointment patches, solutions (suspensions, emulsions, lotions, etc.), cataplasms, tapes, powders for external use, and aerosols, can be used.

All can be used as far as they are an ingredient used for the usual external preparations as an ingredient for the external preparations containing acetylsalicylic acid of the present invention.

In case of ointments, creams, gels and lotions, bases, such as white petrolatum, yellow petrolatum, lanolin, white beeswax, cetyl alcohol, stearyl alcohol, stearic acid, hydrogenated oil, hydrocarbon gel, polyethylene glycols, liquid paraffin and squalane; solvents and solubilizing agents, such as oleic acid, isopropyl myristate, glyceril triisooctanoate, crotamiton, diethyl sebacate, diisopropyl adipate, hexyl laurate, a fatty acid, a fatty acid ester, an aliphatic alcohol and a vegetable oil; antioxidants, such as a tocopherol derivative, L-ascorbic acid, dibutylhydroxytoluene, and butylated hydroxyanisole; antiseptics such as p-hydroxybenzoate; humectants, such as glycerin, propylene glycol, and hyaluronate sodium; surface active agents, such as a polyoxyethylene derivative, glycerol ester of a fatty acid, sucrose ester of a fatty acid, sorbitan ester of a fatty acid, propylene glycol ester of a fatty acid, and lecithin; thickening agents, such as carboxy vinyl polymer, xanthan gum, carboxymethyl cellulose, carboxymethylcellulose sodium, hydroxypropylcellulose, and hydroxypropyl methylcellulose; propellants, such as liquefied petroleum gas, liquefied carbon dioxide, dimethyl ether, nitrogen, kerosene, and carbon dioxide; stabilizers; preservatives; absorption enhancers, and other suitable excipients can be blended therein.

In case of cataplasms, tackifiers, such as polyacrylic acid and polyacrylic acid copolymer; crosslinking agents, such as aluminium sulfate, aluminium potassium sulfate, aluminium chloride, magnesium aluminometasilicate and dihydroxy aluminium acetate; thickening agents, such as sodium polyacrylate, polyvinyl alcohol, polyvinylpyrrolidone, gelatin, sodium alginate, carboxymethyl cellulose, carboxymethylcellulose sodium, hydroxypropylcellulose and hydroxypropyl methylcellulose; polyhydric alcohol such as glycerin, polyethylene glycols (macrogole), propylene glycol, and 1,3-butanediol; surface active agents such as a polyoxyethylene derivative; flavors such as 1-menthol; antiseptics such as p-hydroxybenzoate; purified water; and other suitable excipients can be blended therein.

In case of tapes, adhesives, such as styrene isoprene styrene block copolymer and an acrylic resin; tackifiers, such as alicyclic saturated-hydrocarbon resin, rosin resin, and terpene resin; softeners, such as liquid rubber and liquid paraffin; antioxidants such as dibutylhydroxytoluene; polyhydric alcohols such as propylene glycol; absorption enhancers such as oleic acid; surface active agents such as a polyoxyethylene derivative; and other suitable excipients can be blended therein. Moreover, by adding a polymer which can contain water such as sodium polyacrylate or polyvinyl alcohol and a small amount of purified water can be prepared aqueous tapes.

In case of external powders, vehicles, such as potato starch, rice starch, corn starch, talc, and zinc oxide, and other suitable excipients can be blended therein.

In case of aerosols, excipients used in ointments, creams, gels, suspensions, emulsions, solutions, lotions, external powders, etc., namely bases, such as white petrolatum, yellow petrolatum, lanolin, white beeswax, cetyl alcohol, stearyl alcohol, stearic acid, hydrogenated oil, hydrocarbon gel, polyethylene glycol, liquid paraffin and squalane; solvents and solubilizing agents, such as oleic acid, isopropyl myristate, diisopropyl adipate, diisopropyl sebacate, glyceryl triisooctanoate, crotamiton, diethyl sebacate, hexyl laurate, a fatty acid, a fatty acid ester, an aliphatic alcohol, and a vegetable oil; antioxidants, such as a tocopherol derivative, L-ascorbic acid, dibutylhydroxytoluene, and butylated hydroxyanisole; antiseptics such as p-hydroxybenzoate; humectants, such as glycerin, propylene glycol, and hyaluronate sodium; surface active agents, such as a polyoxyethylene derivative, glycerol ester of a fatty acid, sucrose ester of a fatty acid, sorbitan ester of a fatty acid, propylene glycol of a fatty acid, and lecithin; stabilizers such as thickening agents, such as carboxy vinyl polymer, xanthan gum, carboxymethyl cellulose, carboxymethylcellulose sodium, hydroxypropylcellulose, and hydroxypropyl methylcellulose; vehicles, such as potato starch, rice starch, corn starch, talc, and zinc oxide; propellants, such as liquefied petroleum gas, liquefied carbon dioxide, dimethyl ether, nitrogen, kerosene, and carbon dioxide; buffers; correctives, suspending agents, emulsifiers, perfumes, preservatives, solubilizing agents, and other suitable excipients can be blended therein.

The external preparations of the present invention are manufactured using the conventional procedure for external preparations such as well blending each component and if necessary a base. They are used by applying them in usual methods to the affected region directly, or they are suspended on or immersed in cloth, etc. to apply them to the affected region.

In order to prepare ointments, by using fat, fatty oil, lanolin, wax, resin, plastics, glycol, a higher alcohol, glycerin, water, an emulsifier, a suspending agent or other suitable excipient as a raw material, or by using these materials as a base, an active ingredient is added thereto, and the mixture is homogenously blended to prepare ointments. The base is melted by heating to mix uniformly, and if necessary an additive, such as an absorption enhancer, an antioxidant, an antiseptic, a surface active agent or purified water is added thereto, and further fine powders of the active ingredient are blended with it to prepare ointments or creams.

For example, in order to prepare oleaginous ointments, after melting by warming a base, mixing and cooling halfway, the active ingredients other than the base which are liquefied or made fine powders are mixed with part of the base, and the base remaining is added thereto. The resulting mixture is kneaded together until all parts become homogenous.

For example, in order to prepare emulsion-ointments and water soluble ointments, after a solid base being melted on a water bath, it is kept at about 75° C., and water in which a water-soluble base is dissolved, is warmed to this temperature or a little higher temperature, is added thereto. Then the mixture was homogenously blended to prepare them.

In order to prepare cataplasms, the active agents are previously mixed with an ointment base mainly containing a water soluble polymer which is rich in water retention, such as gelatin, carmellose sodium, methylcellulose, and sodium polyacrylate, and the mixture was expanded on a support such as an unwoven fabric, a surface of the base is covered with a plastic film, such as polyethylene or polypropylene, and it is cut in a desired size to prepare poultices.

In order to prepare tapes, to adhesives such as acrylic resin, or styrene isoprene styrene block copolymers are added tackfiers such as alicyclic saturated-hydrocarbon resin, such as rosin resin and terpene resin, softeners such as liquid rubber, and liquid paraffin, absorption enhancers, an antioxidant, etc., and the mixture is dissolved in an organic solvent, such as toluene. The mixture was blended or melted under heating and blended, and thereto were added liquefied or powdered active ingredients. The mixture was expanded on a release paper, and when the tape is a soluble type, after expanding and drying, it is laminated with a flexible support, such as a polyurethane film, a polyethylene film, a poly chlorination vinyl film, a woven fabric, and an unwoven fabric, and it is cut in a desired size to prepare tapes.

In order to prepare lotions, an active ingredient, a solvent, an emulsifier, a suspending agent, etc. are added to an aqueous liquid, and the mixture is made homogenous. In regard to suspension-lotions, after an active ingredient is pulverized and is made easy to wet in water by glycerin or ethanol, a solution of a suspending agent or a lotion base is gradually added thereto, and the mixture is homogenously blended to prepare suspension-lotions. In regard to emulsion-lotions, an oil-soluble drug and an oil phase are put into one container, and the aqueous phase is put into the other container, and both containers are warmed. In case of making an O/W emulsion, an oil phase is gradually added to an aqueous phase, and in case of making a W/O emulsion, an aqueous phase is gradually added to an oil phase on the contrary, and the mixture continues mixing until emulsification is completely homogenized and serves as a homogeneous liquid.

In order to prepare external powders, an active ingredient, an additive and excipients such as potato starch, rice starch, corn starch, talc, and zinc oxide, are uniformly dispersed.

In order to prepare aerosols, solutions containing an active ingredient, ointments, creams, gels, suspensions, emulsions, solutions, lotions, external powders, etc. are prepared in accordance of the above mentioned methods and they are filled into a well-closed container with liquefied gas or compressed gas.

As skin wound accompanied with the pain which is the treatment target of the external preparations of the present invention, for example, temperature impairment, such as burn, thermal burn, thermal-burn ulcer, and frostbite; traumata, such as laceration, excoriation, incised wound, stab wound, contused wound and bite; vessel and thromboangitis, such as Buerger's disease, lymphedema and crus ulcer; postoperative wound, such as wound by dermatome, and surgical wound; bedsore; decubital ulcer; diabetic ulcer; necrosis; ulcer after herpes; medicine ulcer; ostomy; temperature impairment; radiation injury; chemical impairment; and others, etc. are mentioned.

Hereafter, although by illustrating examples and test examples on external preparations of this invention containing acetylsalicylic acid, the present invention should not be limited to these examples.

EXAMPLES 1 TO 7 (OINTMENTS)

According to the formulation shown in Table 1, acetylsalicylic acid was added to the mixture of bases and solvents, and the mixture was well kneaded under stirring to prepare ointments.

TABLE 1

Formulation of ointments containing acetylsalicylic acid

| Ingredient | Example 1 | 2 | 3 | 4 | 5 | 6 | 7 |
|---|---|---|---|---|---|---|---|
| | Ingredient ratio (% by weight) | | | | | | |
| Acetylsalicylic acid | 0.1 | 2.0 | 10.0 | 5.0 | 5.0 | 5.0 | 5.0 |
| Crotamiton | 2.5 | 2.5 | 2.5 | | | | |
| Polysorbate 80 | | | | 5.0 | | | |
| Sesame oil | | | | | 5.0 | | |
| Diisopropyl adipate | | | | | | 5.0 | |
| Isopropyl myristate | | | | | | | 5.0 |
| White petrolatum | 97.4 | 95.5 | 87.5 | | | | |
| Hydrocarbon gel | | | | 90.0 | 90.0 | 90.0 | 90.0 |

EXAMPLE 8 (SOLUTIONS)

According to the formulation shown in Table 2, acetylsalicylic acid was dissolved or dispersed in a solvent, and the mixture was added under vigorous stirring to warmed purified-water in which other ingredients were dissolved, and the mixture was blended until it became homogenous to prepare solutions.

TABLE 2

Formulation of a solution containing acetylsalicylic acid

| Ingredient | Example 8 Ingredient ratio (% by weight) |
|---|---|
| Acetylsalicylic acid | 0.5 |
| Crotamiton | 1.0 |
| Squalane | 3.0 |
| Cetyl alcohol | 3.0 |
| Sorbitan sesquioleate | 0.5 |
| Polyoxy(20)cetyl ether | 1.5 |
| Propylene glycol | 5.0 |
| Triethanolamine | 0.4 |
| Purified water | 85.1 |

EXAMPLES 9 AND 10 (GELS)

In accordance of the formulation shown in Table 3, after a water soluble polymer was warmed to melt, thereto was added acetylsalicylic acid which was dispersed or dissolved in the solvent and remaining bases. The mixture was stirred until it became homogenous to prepare gels.

TABLE 3

Formulation of gels containing acetylsalicylic acid

| Ingredient | Example 9 | 10 |
|---|---|---|
| | Ingredient ratio (% by weight) | |
| Acetylsalicylic acid | 0.1 | 5.0 |
| Crotamiton | 5.0 | |
| Isopropanol | | 5.0 |
| Propylene glycol | 45.0 | 45.0 |
| Polyacrylic acid | 25.0 | 25.0 |
| Triethanolamine | 0.7 | 0.7 |
| Purified water | 24.2 | 19.3 |

EXAMPLES 11 AND 12 (CREAMS)

According to the formulation shown in Table 4, after oil base being melted on a water bath, thereto was added acetylsalicylic acid which was dissolved or dispersed in a solvent. Thereto was added an aqueous base which was dissolved in water and warmed. The mixture was blended until it became homogenous to prepare creams.

TABLE 4

Formulation of creams containing acetylsalicylic acid

| | Example | |
|---|---|---|
| | 11 | 12 |
| Ingredient | Ingredient ratio (% by weight) | |
| Acetylsalicylic acid | 0.5 | 1.0 |
| Crotamiton | 2.5 | |
| Sesame oil | | 5.0 |
| Diisopropyl sebacate | 2.5 | |
| Cetyl alcohol | 9.0 | 9.0 |
| White petrolatum | 8.0 | 8.0 |
| Hexyl decanol | 1.0 | 1.0 |
| Polyethylene glycol monostearate | 2.0 | 2.0 |
| Polyoxy(9)lauryl ether | 2.8 | 2.8 |
| Polyoxy(23)cetyl ether | 2.0 | 2.0 |
| Propylene glycol | 12.0 | 12.0 |
| Methylparaben | 0.1 | 0.1 |
| Propylparaben | 0.1 | 0.1 |
| Purified water | 57.5 | 57.0 |

EXAMPLE 13 (TAPES)

In accordance with the formulation shown in Table 5, a tackifier, a softener, a solvent, an absorption enhancer, an antioxidant, etc. were added to adhesives and the mixture was dissolved or melted in an organic solvent such as toluene. To the mixture was added under stirring acetylsalicylic acid. This mixture was expanded on a release paper, and in case of a dissolved type, after expansion and drying, it was laminated together with a flexible support and cut in a desired size to give tapes.

TABLE 5

Formulation of a tape containing acetylsalicylic acid

| Ingredient | Example 13<br>Ingredient ratio (% by weight) |
|---|---|
| Acetylsalicylic acid | 20.0 |
| Crotamiton | 5.0 |
| Styrene isoprene styrene block copolymer | 16.7 |
| Alicyclic saturated-hydrocarbon resin | 32.8 |
| Polybutene | 13.3 |
| Liquid paraffin | 11.2 |
| Dibutylhydroxytoluene | 1.0 |

EXAMPLE 14 (POWDERS)

According to the formulation shown in Table 6, potato starch, zinc oxide, and acetylsalicylic acid were blended well until it became homogenous to prepare powders.

TABLE 6

Formulation of a powder containing acetylsalicylic acid

| Ingredient | Example 14<br>Ingredient ratio (% by weight) |
|---|---|
| Acetylsalicylic acid | 0.5 |
| Potato starch | 95.5 |
| Zinc oxides | 4.0 |

COMPARATIVE EXAMPLES 1-3

As shown in Table 7, Commercialized product A (nonsteroidal anti-inflammatoric and analgesic external preparation), and Commercialized products B and C (external preparations for treatment of skin wound) were used as comparative compounds.

TABLE 7

Formulation of commercialized products in comparative examples

| | Comparative example | | |
|---|---|---|---|
| | 1 | 2 | 3 |
| Commercialized product | A | B | C |
| Active ingredient (% by weight) | Indometacin (1.0) | Bucladesine sodium (3.0) | Retinoic acid tocopherol (0.25) |

TEST EXAMPLE

An inhibitory effect to a pain in skin wound region on the external preparations of the present invention for treatment of skin wound accompanied with a pain was conducted using postoperative pain model animals (rat), and a wound-healing effect was tested using wound model animals (rats).

Furthermore, an effect for treatment of skin wound accompanied with a pain by the external preparations of the present invention was tested on volunteers.

TEST EXAMPLE 1

Inhibition Test of Pain Using Postoperative-Pain Model

Surgical operation was performed to a left paw of male rats (eight weeks old; n=12) to produce a postoperative pain model. The rats on which the pain threshold reduced were grouped into by RANDALL-SELITTO-test.

Spreading time of the medicine at this time was set for 15 hours. The control group was set under the same condition as the medication group for spreading time.

The pain threshold was with time measured after removal of the medicine, and the pain threshold ratio was calculated and evaluated from the pain threshold before operation.

Pain threshold ratio=pain threshold at the time of measurement/the pain threshold before treatment (preoperative)×100

The result is shown in Table 8.

TABLE 8

Pain threshold ratio in postoperative pain model

| | | Threshold ratio (%) | |
|---|---|---|---|
| Group | Administered drug (% by weight) | Before administration | After administration |
| Ointment base | | 29.5 | 23.6 |
| Example 3 | Aspirin 10.0 | 28.4 | 67.0 |
| Example 4 | Aspirin 5.0 | 25.3 | 59.1 |
| Example 8 | Aspirin 0.5 | 26.2 | 49.3 |
| Example 13 | Aspirin 20.0 | 26.9 | 58.1 |
| Comparative example 1 | Indomethacin 1.0 | 25.9 | 45.5 |

From the result shown in Table 8, in a postoperative pain model, Examples 3, 4, 8 and 13 containing aspirin showed higher pain threshold ratio compared with the comparative example and the ointment base. A higher pain-inhibition effect was confirmed on the preparations containing aspirin.

TEST EXAMPLE 2

Wound-Healing Test Using Rat Deficit Crack Model

After removal of hairs on the back of male rats (ten weeks old; n=10), deficit crack model was produced. The medicament was repeatedly applied for 15 days to the affected part, and the area of deficit part was measured with time.

The result is shown in Table 9.

TABLE 9

Changes of affected part area in deficit crack model

| | | Affected part area (%) | | |
|---|---|---|---|---|
| Group | Administered drug (% by weight) | Before administration | 7th day | 15th day |
| Ointment base | | 100 | 94 | 11 |
| Example 1 | Aspirin 0.1 | 100 | 53 | 3 |
| Example 5 | Aspirin 5.0 | 100 | 46 | 4 |
| Example 10 | Aspirin 5.0 | 100 | 60 | 8 |
| Example 11 | Aspirin 0.5 | 100 | 58 | 6 |
| Comparative example 1 | Indomethacin 1.0 | 100 | 114 | 72 |
| Comparative example 2 | Bucladesine sodium 3.0 | 100 | 65 | 5 |
| Comparative example 3 | Retinoic acid tocopherol 0.25 | 100 | 72 | 9 |

From the result shown in Table 9, Examples 1, 5, 10 and 11 containing aspirin, respectively reduced the deficit area compared with the ointment base, and reduced the deficit area more than equivalent compared with Comparative examples 2 and 3. On the other hand, Comparative example 1 which is a commercialized analgesic external preparation, hardly reduced the deficit area, and the reduction of the deficit area was almost equivalent to that of the ointment base.

TEST EXAMPLE 3

Wound-Healing Test Using Rat Thermal-Burn Model

After removal of hairs on the back of male rats (ten weeks old; n=10), thermal-burn model was produced. The medicine was repeatedly applied to the affected part for 25 days, and the thermal-burn area was measured with time.

The result is shown in Table 10.

TABLE 10

Changes of affected part area in thermal-burn model

| | | Affected part area (%) | | |
|---|---|---|---|---|
| Group | Administered drug (% by weight) | Before administration | 13th day | 25th day |
| Ointment base | | 100 | 129 | 19 |
| Example 2 | Aspirin 2.0 | 100 | 71 | 9 |
| Example 7 | Aspirin 5.0 | 100 | 68 | 4 |
| Example 9 | Aspirin 0.1 | 100 | 67 | 8 |
| Example 14 | Aspirin 0.5 | 100 | 65 | 13 |
| Comparative example 1 | Indomethacin 1.0 | 100 | 146 | 83 |
| Comparative example 2 | Bucladesine sodium 3.0 | 100 | 113 | 18 |
| Comparative example 3 | Retinoic acid tocopherol 0.25 | 100 | 82 | 38 |

From the result shown in Table 10, earlier reduction of the thermal-burn area in Examples 2, 7, 9 and 14 containing aspirin, respectively, was confirmed compared with the ointment base and Comparative examples 2 and 3. On the other hand, in Comparative example 1 which was a commercialized analgesic external preparation, reduction of the thermal-burn area was hardly seen, and the reduction of the deficit area was almost equivalent to that of the ointment base.

TEST EXAMPLE 4

Improvement to a Pain of Thermal-Burn Patients (Degree I-II)

An external preparation containing aspirin was applied to 15 thermal-burn patients with a pain (total number) and evaluation on the improvement to the pain was conducted.

The improvement of the pain was evaluated in following five step-standard, A: markedly effective, B: effective, C: slightly effective, D: no change, and E: worse.

In case of slightly effective or more than slightly effective, the cases were judged to be effective, and the effectiveness was calculated.

The result is shown in Table 11.

TABLE 11

Improvement to pain of thermal-burn patient

| Group | Administered drug (% by weight) | Number of patient | Evaluation A | B | C | D | E | Effective rate (%) |
|---|---|---|---|---|---|---|---|---|
| Ointment base | | 4 | 0 | 0 | 0 | 3 | 1 | 0 |
| Example 6 | Aspirin 5.0 | 4 | 1 | 1 | 2 | 0 | 0 | 100 |
| Example 12 | Aspirin 1.0 | 3 | 1 | 1 | 0 | 1 | 0 | 67 |
| Comparative example 3 | Retinoic acid tocopherol 0.25 | 4 | 0 | 0 | 2 | 1 | 1 | 50 |

From the result of Table 11, it was confirmed that Examples 6 and 12 containing aspirin more controlled a pain of thermal-burn patients compared with the ointment base and Comparative example 3.

Thus, a steroid and a nonsteroidal anti-inflammatory and analgesic agent are usually said to retard skin wound-healing by their medication to the skin wound region. Retardation of skin wound-healing on these medicines was observed also in the above-mentioned test result.

Industrial Applicability

According to the present invention by containing acetylsalicylic acid, or its pharmacologically acceptable derivative or salt as an active ingredient in the preparation, in skin wound accompanied with a pain, (such as traumata, e.g., thermal burn, racoma, laceration, and incised wound, infectious disease in surgery, postoperative wound, decubital ulcer, temperature impairment, chemical impairment, radiation injury, and vessel and lymphangiopathy), the external preparations for treatment of painful skin wound, which has an outstanding therapeutic effect on the skin wound and an alleviation effect on a pain of the wound part can be offered.

The invention claimed is:

1. A method for treating a skin wound and for alleviating pain associated with a skin wound which consists of administering to an affected part of a patient having the skin wound an effective dose of a medicine containing as an active ingredient acetylsalicylic acid, in a concentration of 0.1 to 5% by weight, and at least one carrier selected from the group consisting of crotamiton, sesame oil, isopropyl myristate, diisopropyl adipate, polyethylene glycol, hydrocarbon gel and white petrolatum, wherein said skin wound is selected from the group consisting of infectious disease in surgery, and vessel and lymphangiopathy.

2. A method for treating a skin wound and for alleviating pain associated with a skin wound which consists of administering to an affected part of a patient having the skin wound an effective dose of a medicine containing as an active ingredient acetylsalicylic acid, in a concentration of 0.1 to 5% by weight, and at least one carrier selected from the group consisting of crotamiton, sesame oil, isopropyl myristate, diisopropyl adipate, polyethylene glycol, hydrocarbon gel and white petrolatum, wherein said skin wound is selected from the group consisting of infectious disease in surgery, and vessel and lymphangiopathy, and wherein the medicine does not retard wound-healing.

* * * * *